United States Patent [19]
Casper et al.

[11] Patent Number: 5,988,163
[45] Date of Patent: *Nov. 23, 1999

[54] DRY POWDER MEDICAMENT INHALATOR HAVING AN INHALATION-ACTIVATED FLOW DIVERTING MEANS FOR TRIGGERING DELIVERY OF DELIVERY OF MEDICAMENT

[75] Inventors: Robert A. Casper, Raleigh; Frank A. Leith; David L. Gardner, both of Chapel Hill, all of N.C.

[73] Assignee: Innovative Devices, Raleigh, N.C.

[ * ] Notice: This patent is subject to a terminal disclaimer.

[21] Appl. No.: 09/076,255

[22] Filed: May 11, 1998

Related U.S. Application Data

[60] Division of application No. 08/823,139, Mar. 25, 1997, Pat. No. 5,823,183, which is a continuation-in-part of application No. 08/690,989, Aug. 1, 1996, Pat. No. 5,692,496
[60] Provisional application No. 60/011,786, Feb. 16, 1996.

[51] Int. Cl.$^6$ .................................................. A61M 15/00
[52] U.S. Cl. ................................. 128/203.15; 128/203.21
[58] Field of Search ........................ 128/203.12, 203.15, 128/203.21; 604/58

[56] References Cited

U.S. PATENT DOCUMENTS

| | | | |
|---|---|---|---|
| 3,807,400 | 4/1974 | Cocozza | 128/203.21 |
| 3,906,950 | 9/1975 | Cocozza | 128/203.21 |
| 3,921,637 | 11/1975 | Bennie et al. | 128/203.15 |
| 3,991,761 | 11/1976 | Cocozza | 128/203.21 |
| 4,013,075 | 3/1977 | Cocozza | 128/203.21 |
| 4,627,432 | 12/1986 | Newell et al. | 128/203.15 |
| 4,664,107 | 5/1987 | Wass | 128/200.23 |
| 4,667,668 | 5/1987 | Wetterlin | 128/203.15 |
| 4,668,218 | 5/1987 | Virtanen | 604/58 |
| 4,805,811 | 2/1989 | Wetterlin | 222/337 |
| 5,033,463 | 7/1991 | Cocozza | 128/203.21 |
| 5,161,524 | 11/1992 | Evans | 128/203.15 |
| 5,201,308 | 4/1993 | Newhouse | 128/203.15 |
| 5,320,714 | 6/1994 | Brendel | 128/203.15 |
| 5,327,883 | 7/1994 | Williams et al. | 128/203.12 |
| 5,347,999 | 9/1994 | Poss et al. | 128/203.15 |
| 5,388,572 | 2/1995 | Mulhauser et al. | 128/203.15 |
| 5,408,994 | 4/1995 | Wass et al. | 128/200.23 |
| 5,437,271 | 8/1995 | Hodson et al. | 128/203.15 |
| 5,447,151 | 9/1995 | Bruna et al. | 128/203.15 |
| 5,482,032 | 1/1996 | Smith et al. | 128/203.15 |
| 5,483,954 | 1/1996 | Mecikalski | 128/203.15 |
| 5,622,166 | 4/1997 | Eisele et al. | 128/203.12 |
| 5,692,496 | 12/1997 | Casper et al. | 128/203.15 |
| 5,823,183 | 10/1998 | Casper et al. | 128/203.15 |

FOREIGN PATENT DOCUMENTS

| | | |
|---|---|---|
| 0 211 595 A2 | 7/1986 | European Pat. Off. . |
| 0 455 463 A1 | 4/1991 | European Pat. Off. . |
| 0 467 172 A1 | 7/1991 | European Pat. Off. . |
| 40 20 571 A1 | 6/1990 | Germany . |
| 41 33 274 A1 | 10/1991 | Germany . |
| 2 165 159 | 10/1985 | United Kingdom ............. 128/203.15 |
| WO 90/13328 | 4/1990 | WIPO . |
| WO 93/12831 | 12/1992 | WIPO . |

*Primary Examiner*—Aaron J. Lewis
*Attorney, Agent, or Firm*—Thorpe, North & Western, LLP

[57] ABSTRACT

An inhalation-activated inhalator having a primary inhalation passage and a secondary inhalation passage disposed in communication with the primary inhalation passage and a source of medicament. The primary inhalation passage has a flow inhibiting mechanism connected to a blocking plate positioned to selectively block fluid flow between the secondary and primary inhalation passage. As the user's inhalation reaches a defined rate, the flow inhibiting mechanism restricts flow through the primary inhalation passage and moves the blocking plate to enable airflow through the secondary passage. Thus, as the user achieves a desired inhalation rate, the medicament is provided through the secondary inhalation passage, thereby optimizing the delivery of medicament to the lungs.

25 Claims, 5 Drawing Sheets

DRY POWDER MEDICAMENT INHALATOR HAVING AN INHALATION-ACTIVATED FLOW DIVERTING MEANS FOR TRIGGERING DELIVERY OF DELIVERY OF MEDICAMENT

RELATED APPLICATIONS

This application is a divisional application of U.S. application Ser. No. 08/823,139, filed Mar. 25, 1997, now U.S. Pat. No. 5,823,183, which is a continuation-in-part application of U.S. application Ser. No. 08/690,989, filed Aug. 1, 1996, now U.S. Pat. No. 5,692,496, which claimed benefit of an application filed under 35 U.S.C. §111(a) for an invention which was disclosed in Provisional Application Serial No. 60/011,786, filed under 35 U.S.C. §111(b) on Feb. 16, 1996.

FIELD OF THE INVENTION

The present invention relates to an improved medicament inhalator. More particularly, the present invention relates to a dry powder medicament inhalator usable by asthmatics and the like in such a manner to facilitate proper deposition of the medicament in the lungs. By inhaling on a mouthpiece, a prescribed dosage of medicament becomes available to the patient during the proper portion of inspiration to maximize deposition in the lungs of the user.

STATE OF THE ART

The widespread existence of asthma and other respiratory disorders which inhibit proper breathing has lead to the development of numerous medications which can be used to open restricted breathing passages and enable the user to breathe more freely. Some asthmatics suffer from only occasional attacks. For others, however, breathing is a constant struggle which would be nearly impossible without the appropriate medication. These medications may be in either dry or liquid form, depending on the type of medication.

There are essentially two types of inhalation devices currently available in the marketplace for the administration of a medicament to the lungs. The predominant inhalation device is a pressurized, metered dose inhaler containing a suspension of drug in a pharmaceutically inert liquid propellant, e.g., chlorofluorocarbons or fluorocarbons. Inhalation devices of this type are well known in the art and are commonly used.

These propellant-based inhalation devices have the advantage of consistently delivering a predetermined dose of medication from the aerosol canister. However, the drug particles are propelled at high velocity from the inhalation device. A significant quantity of the medication impacts tissue in the mouth or throat of the patient, becoming unavailable for deposition in the lungs. Further, growing concern over the link between depletion of atmospheric ozone and chlorofluorocarbon propellants has focused attention on the development of alternative means of delivering medication to the lungs, including the development of dry powder inhalation systems.

Dry powder inhalers represent the second major type of inhalation devices. Dry powder inhaler devices known to the applicants and existing in the marketplace utilize the patient's inhaled breath as a vehicle to transport the dry powder drug to the lungs. Presently there are four principal methods in use to provide fine particulate powder to the lungs without the use of chlorofluorocarbons or other propellants.

The first method available relies on the use of a hard gelatin capsule which contains a premeasured dose of therapeutically active material and an inhalator device for use with the capsule. The capsule is placed in the inhalator device which serves to open or perforate the capsule, exposing the dose of medicament. The medicament is removed from the capsule, by the vacuum action created when the patient inhales through the mouthpiece of the device, and is entrained in the inspired air stream for transport to the patient's lungs. The empty capsule is removed from the inhalation device after each use.

Inhalators using this type of capsule technology are described in U.S. Pat. Nos. 3,807,400 (Cocozza); 3,906,950 (Cocozza); 3,991,761 (Cocozza) and 4,013,075 (Cocozza). The intent in each of these devices is to remove all of the powdered medicament from the interior of the capsule. However, it has been found that the air stream generated by the patient is typically insufficient to accomplish complete removal of medicament from the capsule. This may be especially true for a patient having an asthma attack. Further, gelatin capsules are affected by relative humidity on storage and may become hydrated, resulting in poor opening of the capsule and agglomeration of the powder contents, or dehydrated, resulting in brittle fracture of the capsule, potentially making fine gelatin fragments available for inhalation or compromising dosing due to electrostatic attraction of medicament to the capsule surfaces.

A second method for delivery of dry powder medicaments relies on providing a package containing multiple doses of medicament, each contained in a sealed blister. The package is used in conjunction with a specially designed inhalation device which provides a means of attachment for the package and perforation of an individual blister by the patient prior to the inhalation of its contents. Delivery systems of this type are described in EPO Patent Application Publication No. 0 211 595 A2 (Newell et al.); EPO Patent Application Publication No. 0 455 463 A1 (Velasquez et al.); and EPO Patent Application Publication No. 0 467 172 A1 (Cocozza et al.). As the patient inhales, a portion of the inhaled air stream flows continuously through the perforated blister entraining the medicament and providing for inclusion of the medicament in the inspired breath. Delivery of medicament to the patient's inspired air stream begins as sufficient flow develops through the blister for removal of the medicament. No means is provided by which the point or rate of delivery of medicament to the patient is controlled.

A third method for delivery of dry powder medicaments involves the use of a device equipped with a drug reservoir containing sufficient medicament for a much larger number of doses. The Draco TURBUHALER® is an example of this type of device and is described in detail in U.S. Pat. No. 4,688,218 (Virtanen); U.S. Pat. No. 4,667,668 (Wetterlin); and U.S. Pat. No. 4,805,811 (Wetterlin). The device provides a means for withdrawing a dose of medicament from the reservoir and presenting the withdrawn dose for inhalation by the patient. As the patient inhales through the mouthpiece of the device, the medicament contained in perforations in a dosing plate is entrained in the inspired air and flows through a conduit or conduits. The conduits serve as a vortex creating a means for breaking up powder agglomerates before the medicament becomes available to the patient. Moisture ingress in the reservoir results in agglomeration of the powder contents, compromising dosing due to retention of powder in the perforations in the dosing plate and potentially inadequate breakup of particulates in the inspired air stream.

A fourth method for delivery of dry powder medicaments involves the use of a piston to provide air for either entraining powdered medicament, lifting medicament from a carrier screen by passing air through the screen, or mixing air with powder medicament in a mixing chamber with subsequent introduction of the powder to the patient through the mouthpiece of the device. Devices of this general type are described in PCT WO 93/12831 (Zirerenberg et al.); German Patent No. DE 4133274 A1 (Kuhnel et al.); German Patent No. DE 4020571 A1 (Hochrainer et al.); and U.S. Pat. No. 5,388,572 (Mulhauser et al.). The incorporation of a piston system, in each case, adds to the complexity of the inhalation device, both in terms of use by the patient and device manufacturability.

Thus, there is a need for an improved medicament inhalator wherein the availability of the medicament is controlled to ensure that the medicament is properly deposited in the lungs. Such a device preferably should be configured to release medicament into the inspired air stream during inhalation when a defined inhalation rate has been achieved. Such a device should also ensure that medicament agglomerations and medicament carried agglomerations are broken up before reaching the patient. In addition, the device should enable repeated use without redosing.

OBJECTS OF THE INVENTION

Thus, it is an object of the present invention to provide a medicament inhalator for the administration of dry powder which controls when the medicament is made available for inhalation, thereby maximizing delivery of the medicament to the lungs. The medicament may be pure drug particles, or may be drug particles attached to a carrier particle, e.g. lactose.

It is another object of the present invention to provide such a medicament inhalator which is easy to use and has multiple dosing capabilities.

It is still another object of the present invention to provide such a medicament inhalator which is mechanically simple, does not require depletable power sources and which is relatively inexpensive.

The above and other objects of the invention are realized in specific illustrated embodiments of medicament inhalator having a body with a primary inhalation passage and a secondary inhalation passage disposed therethrough. The primary inhalation passage is formed by a first inhalation channel having a proximal end and a distal end, and a restricting flap or vane disposed between the distal and proximal ends. The restricting vane is rotatably disposed within the primary inhalation passage to selectively inhibit the flow of air through the first inhalation channel. Thus, as the user inhales, drawing air from the proximal end to the distal end of the first inhalation channel, the rotatable vane rotates into a position to occlude a substantial portion of the channel, thereby limiting flow through the channel.

The secondary inhalation passage is configured to receive a medicament dosing in communication therewith. The secondary inhalation passage includes a second inhalation channel, and the medicament dosing device holds a dose of medicament in fluid communication with the second inhalation channel such that air traveling through the second inhalation channel entrains the medicament for delivery to the patient. The second inhalation channel has a blocking member which is biased in a closed position to selectively prevent airflow therethrough. The blocking member, however, is connected to the rotatable vane disposed in the first inhalation channel.

When the user of the inhalator inhales, the rotatable vane rotates into a position wherein it substantially reduces/ inhibits airflow through the first inhalation channel. This same action overcomes the biasing of the blocking member and allows airflow through the second inhalation channel. As air rushes through the second inhalation channel, the medicament disposed in fluid communication with the second inhalation channel is entrained in the air and carried to the user. Thus, the medicament is provided to the user when the rate of inhalation is sufficient to ensure delivery of the medicament to the user's lungs.

In accordance with one aspect of the invention, the inhalation device provides for the administration of dry powder medicaments by temporarily diverting inspiratory flow from the first (primary) inhalation channel to the second (secondary) inhalation channel. By providing the inhalation device with a second inhalation channel which is sufficiently smaller than the primary inhalation channel and which is nonlinear, airflow through the secondary inhalation channel is relatively vigorous and turbulent when the blocking member is moved out of the blocking position. The vigorous airflow helps to entrain the medicament, while promoting either deagglomeration of the medicament particles, deagglomeration of the medicament/carrier particles or facilitating drug particle removal from the carrier particles. Additionally, the nonlinear second inhalation channel may be formed with a portion specifically configured to form an impact surface(s). As the particles of medicament are forcefully drawn through the second inhalation channel, they collide with the impact surface, thereby breaking up any agglomeration of the medicament particles, any agglomeration of the medicament/carrier particles, or facilitating drug particle removal from the carrier particles.

In accordance with another aspect of the present invention, the medicament inhalator may be configured for use with a medicament disk having a plurality of blisters containing the medicament thereon. At or before the beginning of inhalation, the user presses a lancing mechanism to puncture a blister containing medicament. Preferably, the medicament disk is positioned along the secondary inhalation passage such that at least some of the air drawn through the secondary inhalation passage passes through the blister, thereby ensuring that the medicament is carried to the user.

In accordance with yet another aspect of the present invention, the medicament inhalator may be configured to receive a windable tape. The windable tape is provided with a plurality of dosing units, typically in the form of small blisters filled with medicament along the tape. With each use of the medicament inhalator, the tape is drawn through the inhalator. Once all of the dosing units on the tape have been consumed, the tape is replaced.

In accordance with still another aspect of the present invention, the medicament is provided by a replaceable dosing cartridge which contains bulk powdered medicament in a reservoir. Before or during each use, the dosing cartridge is accessed in such a manner as to provide a desired dose of medicament. The dose is disposed in fluid communication with the secondary inhalation passage so that the medicament will be entrained in air flowing therethrough and be carried to the lungs of the user.

In accordance with a preferred embodiment of the invention, the secondary inhalation passage feeds into a distal portion of the primary inhalation channel, i.e. distally from the rotatable vane. Thus, the user places his or her mouth at the distal end of the primary inhalation channel and inhales. Initially, airflow is exclusively through the primary inhalation channel. However, as the rotatable vane rotates into a blocking or inhibiting position, it significantly occludes airflow from the proximal end to the distal end of the primary inhalation channel. At the same time, movement of the rotatable vane moves the blocking member, thereby allowing airflow through the secondary inhalation passage—dispensing medicament into the distal portion of the primary inhalation channel. During such, the user is obtaining a significant portion of the air inhaled through the secondary inhalation passage. This air carries the medicament to the patient's lungs. The rotatable vane may either continue to rotate, ultimately rotating into a position wherein it no longer provides a significant impediment to flow through the primary inhalation channel, or the rotatable vane may restrict inspiratory air flow until inhalation is completed. When the rotatable vane continues to obstruct airflow through the primary inhalation passage, the user is forced to inhale more slowly and deposition of the medicament in the deep lung is maximized.

Once inhalation is completed, the rotatable vane returns to its original position. Likewise, the blocking member returns to its biased position where it blocks airflow through the secondary inhalation passage.

BRIEF DESCRIPTION OF THE DRAWINGS

The above and other objects, features and advantages of the invention will become apparent from a consideration of the following detailed description presented in connection with the accompanying drawings in which.

DETAILED DESCRIPTION

Reference will now be made to the drawings in which the various elements of the present invention will be given numeral designations and in which the invention will be discussed so as to enable one skilled in the art to make and use the invention. It is to be understood that the following description is only exemplary of the principles of the present invention, and should not be viewed as narrowing the pending claims.

Figure 1:
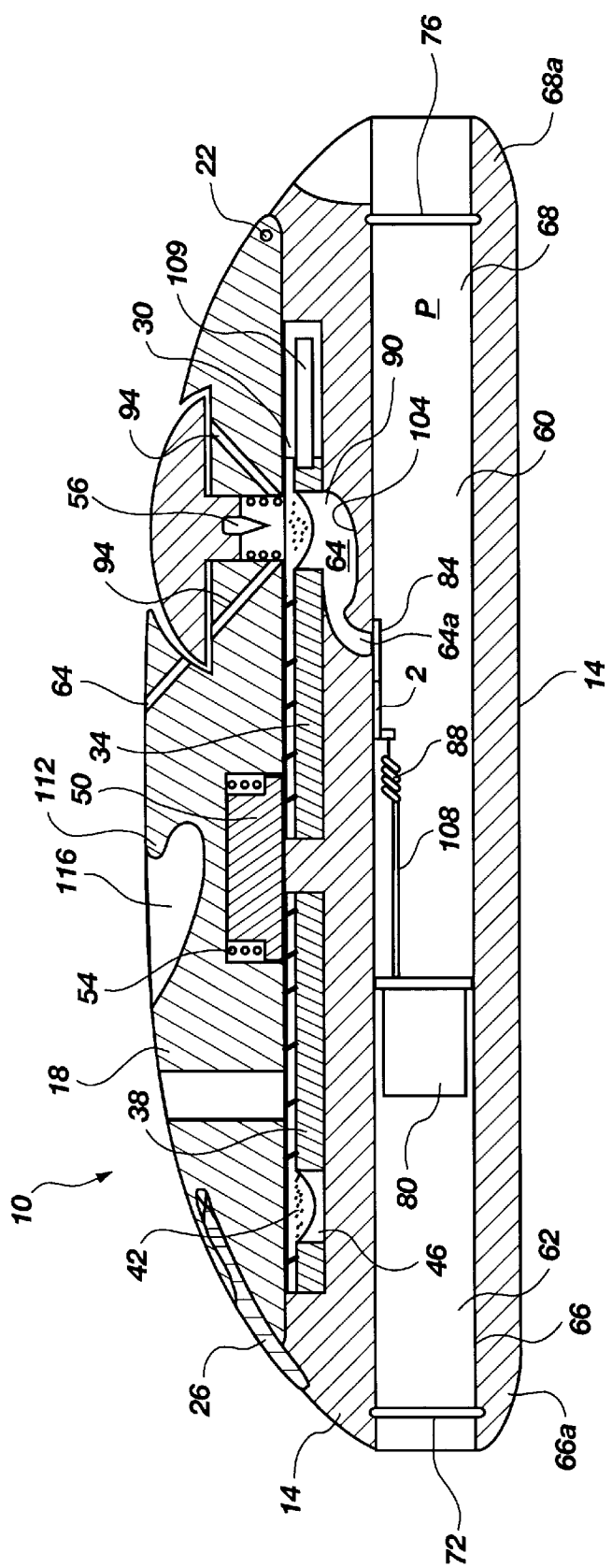
FIG. 1 shows a side cross-sectional view of the medicament inhalator showing the primary and secondary inhalation passages, a medicament dosing disk, a rotatable vane and a blocking member all disposed within the body of the inhalator.
Figure 1A:
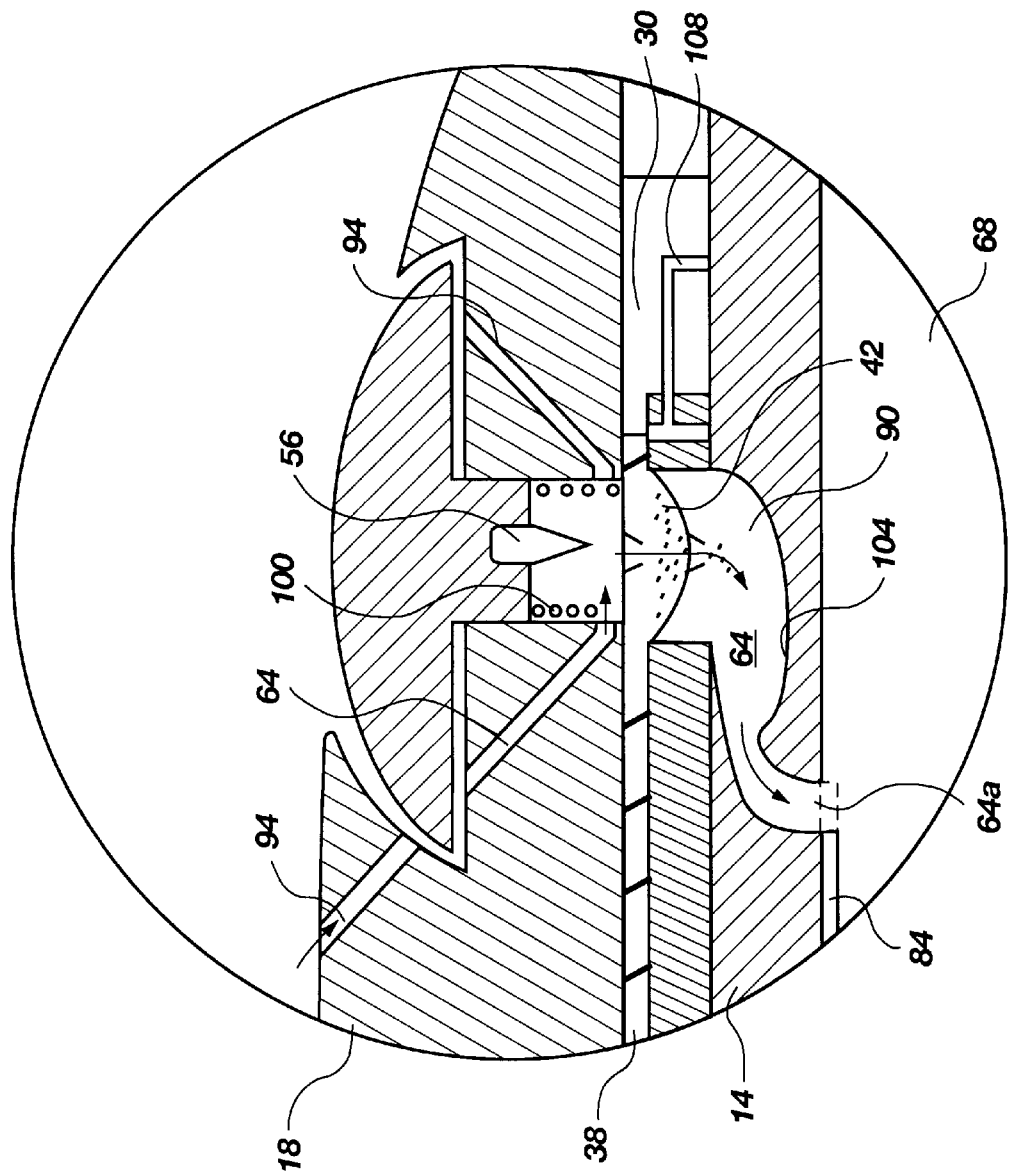
FIG. 1A shows a close-up view of the second inhalation channel and the blocking member.
Figure 1B:
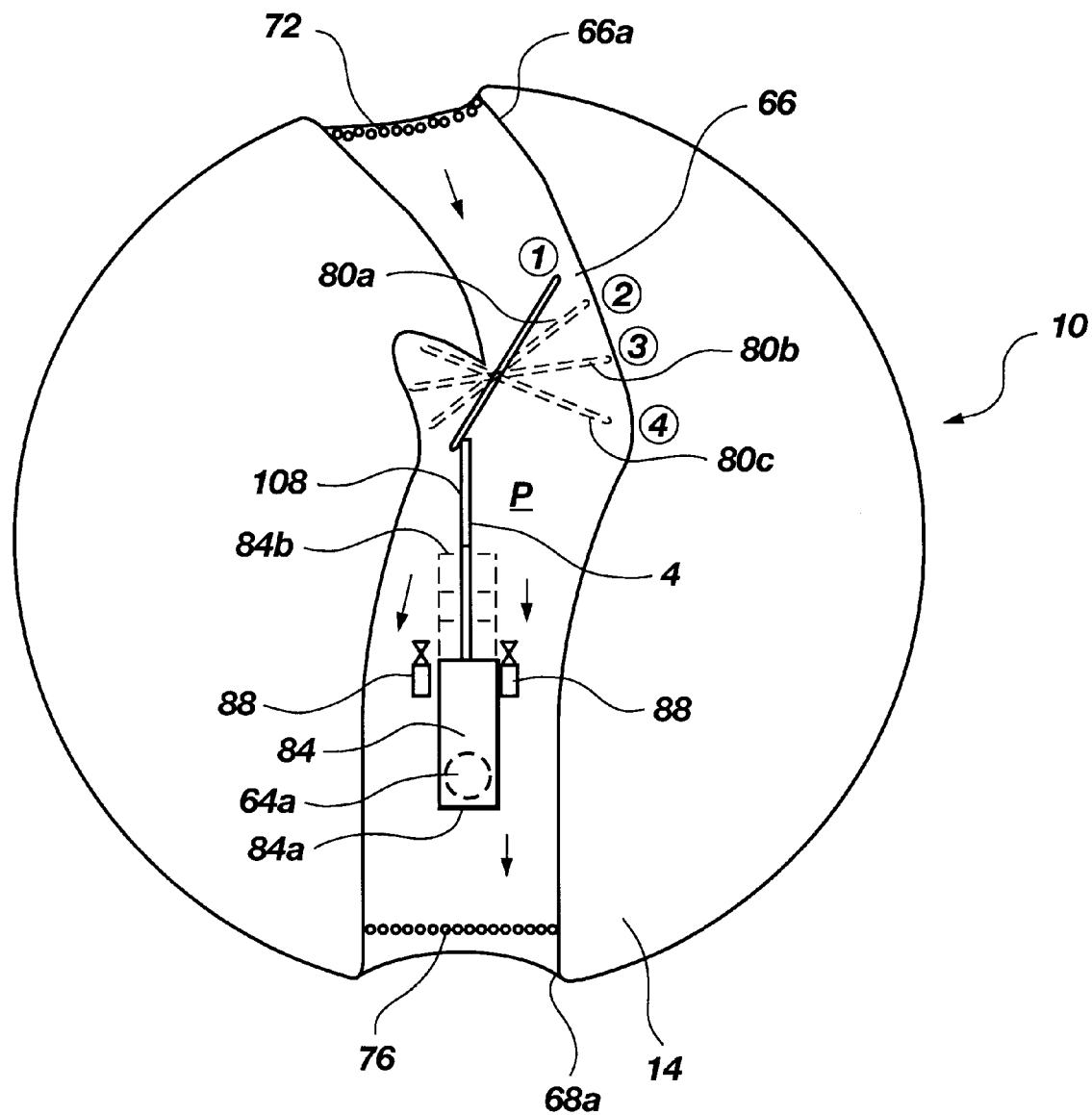
FIG. 1B shows a horizontal cross-sectional view of the inhalator of FIGS. 1 and 1A taken through the primary inhalation passage and looking upwardly.

Referring to FIGS. 1, 1A and 1B, there is shown a side cross-sectional view of a medicament inhalator, generally indicated at 10, for selectively releasing medicament while a user thereof inhales. The medicament inhalator 10 includes a housing with a body 14 and a cover 18. The cover 18, in the embodiment shown in FIG. 1, is attached to the body 14 by a hinge 22. A sliding retention clip 26 is disposed opposite the hinge 22 and disposed to engage the cover 18 to selectively maintain the cover in place.

Disposed between the body 14 and the cover 18 is a cartridge receiving cavity 30 which is configured to receive a cartridge containing medicament. The cartridge receiving cavity 30 has a cartridge receiving plate 34 which is used to support a medicament cartridge 38. Because the medicament cartridge 38 of FIG. 1 is a disk having a plurality of medicament-filled blisters 42, the cartridge receiving plate 34 has an annular channel 46 formed therein in alignment with the blisters of the disk. If desired, the medicament cartridge 38 can also be held in place by a piston 50 which nests in the cover 18, and which is biased toward the body 14 by a spring 54.

The cover 18 also includes a spring loaded lancet 56 which is disposed adjacent the cartridge receiving cavity 30. The lancet 56 is positioned so that, when pressed by the user, the lancet punctures one of the medicament-filled blisters 42 on the medicament cartridge. As will be discussed in detail below, the medicament-filled blister 42 which is penetrated by the lancet 56 is disposed in communication with an inhalation passage which enables the medicament released from the blister to be carried into the lungs of the user.

The medicament inhalator 10 includes a primary inhalation passage 60 which extends through the body 14, and a secondary inhalation passage 64 which extends through the cover 18 and part of the body 14. The secondary inhalation passage 64 terminates in an opening 64a into the primary inhalation passage 60. The various aspects of the secondary inhalation passage 64 will be discussed momentarily.

The primary inhalation passage 60 is formed by an elongate first inhalation channel 62 which extends through the length of the body 14. The first inhalation channel 62 has a proximal portion 66 with a proximal end 66a and a distal portion 68 with a distal end 68a. A screen 72 is disposed at the proximal end 66a and another screen 76 is disposed at the distal end 68a to prevent accidental aspiration of foreign particles.

Disposed between the proximal portion 66 and the distal portion 68 of the primary inhalation channel 60 is a rotatable vane 80. The rotatable vane 80 is disposed so that it may pivot between a first position, indicated at 80a (FIG. 1B), wherein the rotatable vane provides minimal interference to airflow from the proximal end 66a to the distal end 68a of the first inhalation channel 62, and a second position, indicated at 80b, wherein the rotatable vane provides a significant impediment to airflow from the proximal end to the distal end of the first inhalation channel. Movement of the rotatable vane 80 from the first position 80a to the second position 80b is accomplished by airflow created by the user inhaling through the distal end 68a.

The rotatable vane 80 is attached to a blocking plate 84 which is disposed in the first inhalation channel 62 at the opening 64a where the secondary inhalation passage 64 enters into the primary inhalation passage 60. The blocking plate 84 is biased by a spring 88 into a first, closed position (shown in FIG. 1) wherein the blocking plate 84 prevents air from the secondary inhalation passage 64 from flowing into the primary inhalation passage 60. The rotation of the rotatable vane 80 into the second position 80b moves the blocking plate 84 into a second, open position as shown in FIG. 1A. When the blocking plate 84 is in the second, open position, the secondary inhalation passage 64 is disposed in fluid communication with the primary inhalation passage.

When the rotatable vane 80 is disposed in the third position 80c, airflow through the primary inhalation passage 60 is restricted. Thus, the airflow rate through the inhalator 10 is slowed, causing the patient to exert a slow and prolonged effort to inhale. This effort, in turn, maximizes medicament penetration into the deep lung.

Referring specifically to FIG. 1A, there is shown a close-up of the secondary inhalation passage 64 and the structures adjacent thereto. The secondary inhalation passage 64 is formed from a second inhalation channel 90 which extends from the cartridge receiving cavity 30, through part of the body 14, and into the first inhalation channel 62, and at least one third inhalation channel 94 which extends through the cover 18 and into the cartridge receiving cavity 30.

To use the inhalator, the user presses the lancet 56 downward to puncture the medicament-filled blister 42. A spring 100 is disposed below the lancet 56 to return it to its original position. The user then inhales through the primary inhalation passage 60. As the rotatable vane 80 rotates in the first inhalation channel 62 to occlude airflow from the proximal end 66a to the distal end 68a, the rotatable vane 80 slides the blocking plate 84 into the second, open position. Because of the restriction on airflow created by the rotatable vane 80, a vacuum is created in the distal portion 68 of the primary inhalation channel. The movement of the blocking plate 84 into the second, open position enables air to rush through the secondary inhalation passage 64. The air enters the third inhalation channels 94, flows through the punctured medicament-filled blister 42 and then through the second inhalation channel 90. Because of the vigorous airflow which is produced due to the vacuum in the first inhalation channel 62, the medicament is forced out of the medicament-filled blister 42 and into forceful impact with an impaction surface(s) 104. The impaction surface(s) 104 breaks up any agglomeration of the medicament particles, any agglomeration of the medicament/carrier particles, or facilitates drug removal from the carrier particles. This enables the medicament to be carried deeper into the lungs.

After impacting the impaction surface(s) 104, the medicament is carried by the airflow through the opening 64a and into the distal portion of the first inhalation channel 62. The medicament is then carried out through the screen 76 (FIG. 1) and into the user's lungs. Because flow through the secondary inhalation passage 64 is not enabled until the rotatable vane 80 rotates into a second position, the user achieves a defined inhalation flow rate before the medicament is supplied to the user.

Prior to the next use of the medicament inhalator 10, a sliding index advance 109 or some other advancement mechanism is used to rotate the medicament cartridge 38. Rotation of the medicament cartridge 38 places an unused medicament-filled blister 42 beneath the lancet 56 and along the secondary inhalation passage 64.

Once each of the medicament-filled blisters 42 has been used, the cartridge 38 must be replaced. This is accomplished by sliding the retention clip 26, while pulling upwardly on a finger hold 112 formed by a depression 116 in the cover 18. The used disk 38 is removed, and a new disk is inserted into the cavity 30. The cover 18 is then closed and the medicament inhalator is again ready for use.

Referring now to FIG. 1B, there is shown a horizontal cross-sectional view of the medicament inhalator 10 taken through the primary inhalation passage 60 looking upwardly. As shown in FIG. 1B, the rotatable vane 80 is disposed in the first position, indicated at 80a. The blocking plate 84 is disposed in a first, closed position 84a. As the user places the distal end 68a of the body 14 to his or her lips and inhales, the rotatable vane 80 rotates from the first position 84a to the second position 84b, thereby inhibiting airflow from the proximal end 66a to the distal end 68a. The rotation of the rotatable vane 80 moves the blocking plate 84 via a linkage 108, and exposes the opening 64a of the secondary inhalation passage 64. Thus, as the rotatable vane 80 inhibits airflow from the proximal end 66a to the distal end 68a of the first inhalation channel 62, the second inhalation channel 90 is disposed in communication with the distal portion 68 of the first inhalation channel, thereby providing air and medicament for inhalation by the user.

Once the user stops inhaling, the rotatable vane 80 is returned by the spring 88 and linkage 108 to its original position 80a. The spring 88 also moves the blocking plate 84 back into its first, closed position, thereby preventing airflow through the secondary inhalation passage.

By use of the spring's 88 resistance to movement of the rotatable vane 80 and blocking plate 84, the embodiment of the present invention shown in FIGS. 1 through 1B is designed to ensure that the user achieves a defined airflow rate before the medicament is released into the user's lungs. For example, a user will initially inhale at a first rate. The rotation of the rotatable vane 80, however decreases the rate at which the user can inhale to a second, slower rate. Due to the second, slower rate, most of the medicament is insured of reaching deep within the user's lungs, rather than simply being deposited in the mouth or throat of the user. Control over the airflow rate achieved prior to release of the medicament can be achieved by controlling the tension of the spring. Thus, for example, a children's version of the device may use a spring having lower tension than a version configured for adults. The exact tension desired will be easily determinable by those skilled in the art.

Figure 2A:
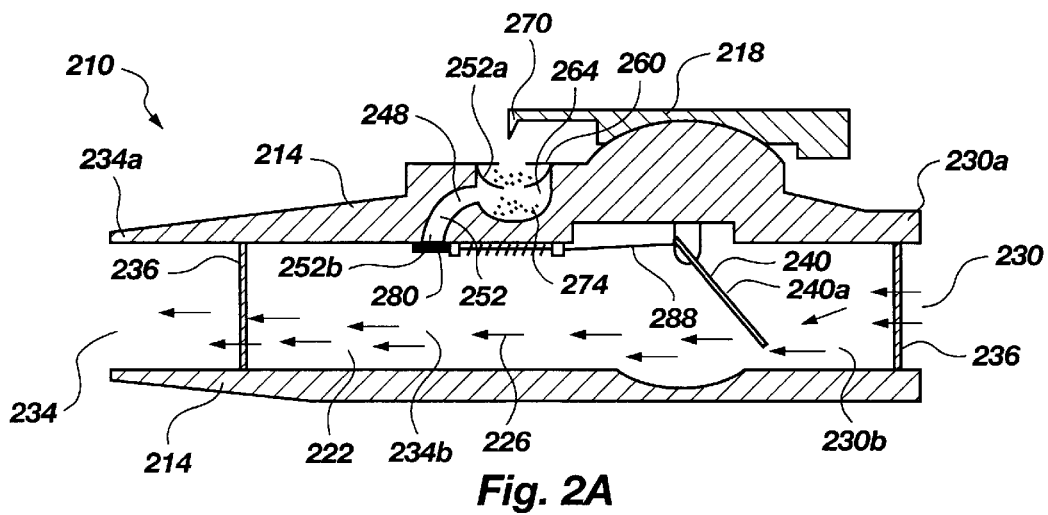
FIG. 2A shows a side cross-sectional view of another embodiment of an inhalator made in accordance with the principles of the present invention, as the embodiment is configured at the beginning of inhalation.

Turning now to FIG. 2A, there is shown a side cross-sectional view of an alternate embodiment of a medicament inhalator, generally indicated at 210, made in accordance with the principles of the present invention. Unlike the embodiment of FIGS. 1 through 1B, the medicament inhalator 210 includes a one-piece housing or body 214 with a lancet 218 pivotably or slidably attached thereto.

A primary inhalation passage 222 is formed in the body 214 of the medicament inhalator 210 by an elongate first inhalation channel 226 which extends from an opening 230 at a proximal end 230a of the body to an opening 234 at a distal end 234a of the body. Screens 236 are disposed adjacent each end to prevent accidental aspiration of foreign particles. The elongate first inhalation channel 226 is divided into a proximal portion 230b and a distal portion 234b by a rotatable vane 240.

The body 214 also includes a secondary inhalation passage 248 which is formed by a second inhalation channel 252 extending from a first opening 252a in the exterior of the body 214, to a second opening 252b into the distal portion 234b of the first inhalation channel 226. The first opening 252a of the second channel 252 is configured for receiving a medicament holding device, such as an elongate tape 260, with a plurality of medicament-filled blisters 264 disposed thereon. The elongate tape 260 is preferentially positioned so that downward pivoting movement of the lancet 218 causes a sharp projection 270 disposed thereon to penetrate through the medicament-filled blister 264 disposed in the first opening 252a of the second inhalation channel 252. As is shown in FIG. 2A, such a puncture enables some of the medicament to fall from the medicament-filled blister 264 to an impact surface 274 disposed along the second inhalation channel 252.

Airflow between the first inhalation channel 226 and the second inhalation channel 252 is selectively prevented by a blocking plate 280 which is biased in a first, closed position wherein the blocking plate covers the second opening 252b in the second inhalation channel. Because any significant airflow through the punctured blister 264 or the secondary inhalation channel 252 is prevented while the blocking plate 280 covers the second opening 252b, the blocking plate 280 must be moved for the medicament to be carried to the user.

To use the medicament inhalator 210, the user places the distal end 234a to his or her mouth and inhales through the opening 234. Initially, the airflow toward the distal end 234a of the elongate first inhalation channel 226 comes exclusively from the proximal end 230a. However, the airflow begins to rotate the rotatable vane 240 out of its original position 240a (FIG. 2A) and into an intermediate, restricting position 240b (FIG. 2B) wherein the rotatable vane 240 obstructs airflow through the elongate first inhalation channel 226. The rotatable vane 240 is connected to the blocking plate 280 via a linkage 288. As the rotatable vane 240 moves into the intermediate position 240b, the linkage 288 moves the blocking plate 280 into a second, open position, wherein the blocking plate no longer covers the opening 252b at the end of the secondary inhalation passage 248. Thus, as air flows through the elongate first inhalation channel 226, the second inhalation channel 252 is opened. Airflow through the first inhalation channel 226 is terminated slightly before airflow through the second inhalation channel 252 is allowed. Airflow through the much smaller second inhalation channel 252 is turbulent and is designed to promote either deaggregation of medicament particles, deaggregation of medicament/carrier particles, or to maximize removal of drug particles from the carrier particles. The airflow is drawn through the medicament-filled blister 264 and entrains the medicament. Any large agglomeration of medicament/carrier particles is caused to forcefully impact against at least one impact surface 274 and is thereby broken into smaller pieces.

Continued inhalation moves the rotatable vane 240 into a final position 240c (FIG. 2C), wherein the rotatable vane 240 still provides interference to airflow through the primary inhalation channel 226. In the final position 240c, the rotatable vane 240 also maintains the blocking plate 280 in the second, open position. Thus, as the user finishes inhalation, air is provided through both the first and second inhalation channels 226 and 252. The overall airflow rate, however, is restricted to below that which was initially enabled when the rotatable vane 240 was in the first position 240a, thereby ensuring prolonged inhalation and improved delivery of medicament to the deep lung. Once the user stops inhalation, the rotatable vane 240 will return to its original position 240a (FIG. 2A) and tape 260 may be advanced to place a new medicament-filled blister 264 in the first opening 252a of the second inhalation channel 252.

Figure 2B:
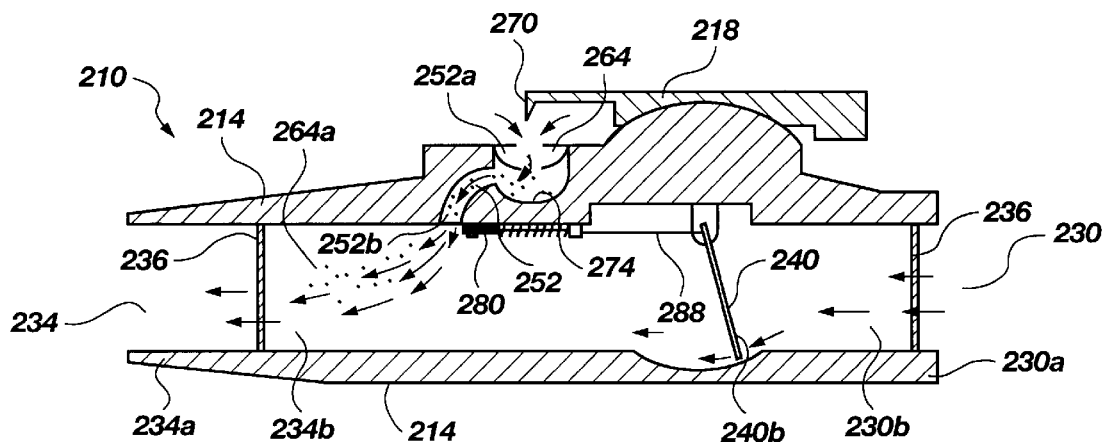
FIG. 2B shows a side cross-sectional view of the embodiment of FIG. 2A, as the medicament inhalator is configured in the middle of inhalation.
Figure 2C:
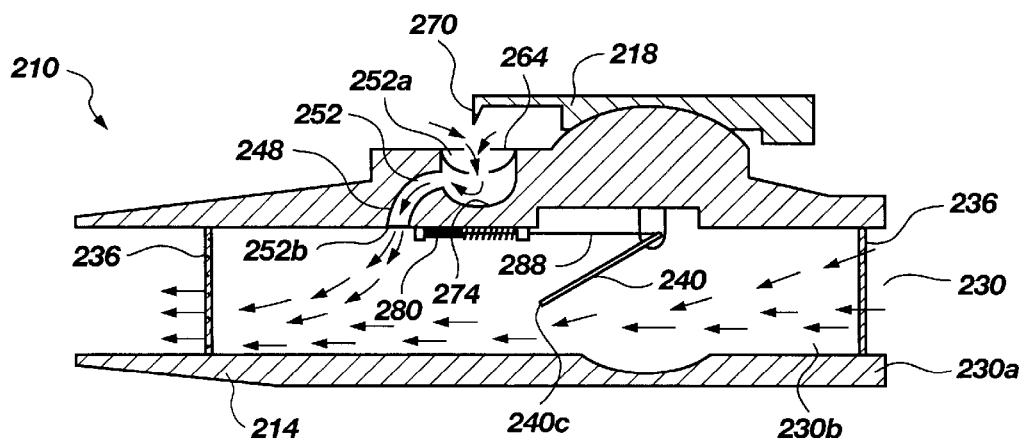
FIG. 2C shows a side cross-sectional view of the embodiment of FIGS. 2A and 2B, as the medicament inhalator is configured near the end of inhalation.

By using the configuration of the medicament inhalator 210 shown in FIGS. 2A through 2C, the medicament is provided to the user at the proper point of the inhalation profile. This ensures better delivery of the medicament to the user's lungs, and thus ensures more efficacious treatment for asthmatics and others with breathing difficulty. At the same time, the device is as simple, if not simpler, to use than the prior art and is mechanically less complex.

Figure 3A:
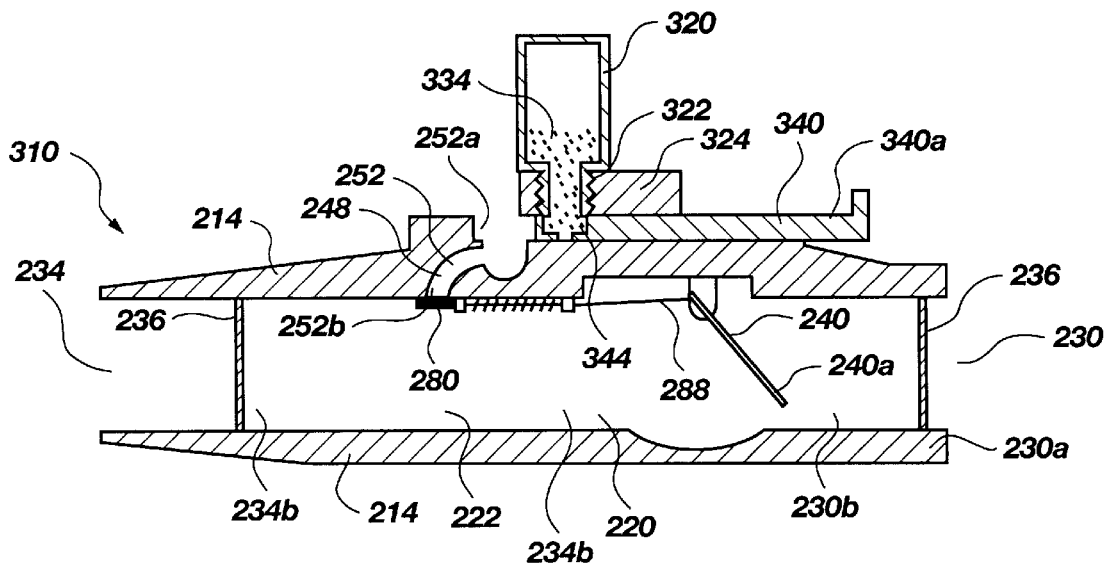
FIG. 3A shows a side cross-sectional view of another embodiment of a medicament inhalator made in accordance with the principles of the present invention, wherein the medicament dosings are provided by a dosing cartridge having a reservoir with bulk medicament disposed therein, and a dosing plunger disposed in a refill position.
Figure 3B:
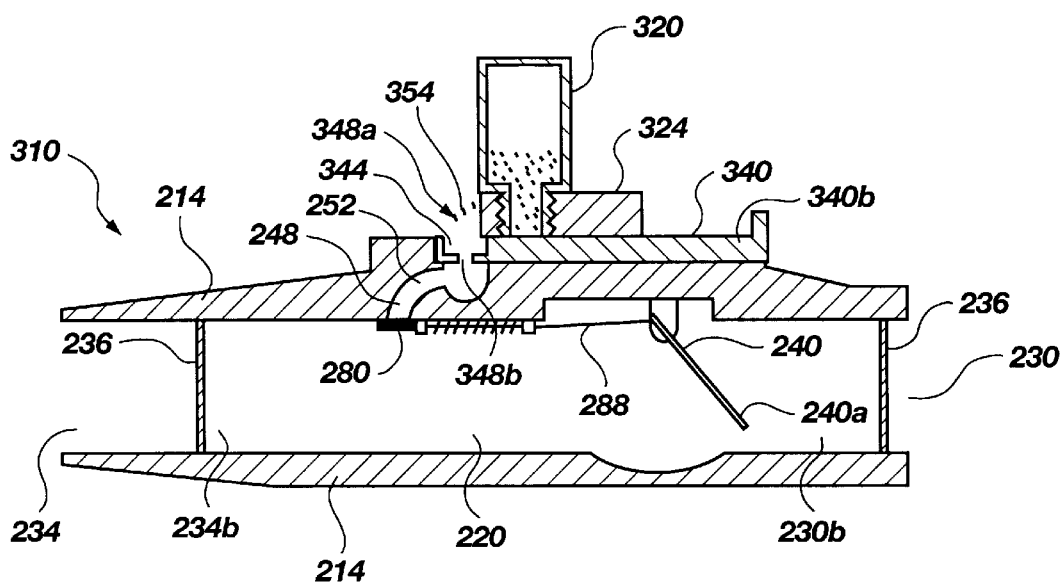
FIG. 3B show a side cross-sectional view of the medicament inhalator of FIG. 3A, with the dosing plunger in a dosing position wherein medicament is supplied to the secondary inhalation passage.

Turning now to FIGS. 3A and 3B, there are shown side cross-sectional views of an alternate embodiment of a medicament inhalator, generally indicated at 310, made in accordance with the principles of the present invention. The medicament inhalator 310 includes a body 214, most of the portions of which are configured the same and function in the same manner as the embodiment shown in FIGS. 2A through 2C. Therefore, such portions are numbered in accordance with the numeral designations used with respect to FIGS. 2A through 2C where appropriate.

The primary difference between the embodiment shown in FIGS. 3A and 3B, compared to that shown in FIGS. 2A through 2C is the manner in which the medicament is provided to the first, upper opening 252a in the secondary inhalation channel 252. Rather than relying on a tape 260 with medicament-filled blisters 264 as discussed in FIGS. 2A through 2C, the embodiment of FIGS. 3A and 3B utilizes a bulk medicament cartridge 320 which is threadedly or otherwise engaged to a cavity 322 in a top portion 324 of the body 214.

In order to dose and distribute the medicament 334 contained within the bulk dosing cartridge 320, a dosing plunger 340 is slidably disposed in the top portion 324 of the housing. The plunger 340 has a dosing chamber 344 disposed therein. The dosing chamber 344 has an upper opening 348a which is sized to receive medicament 334 from the bulk medicament cartridge 320 when the plunger is disposed in a first, refill position, as indicated at 340a in FIG. 3A.

The dosing chamber 344 also has a lower opening 348b disposed opposite the upper opening 348a. When the dosing plunger 340 is in the first, refill position 340a, the lower opening 348b is essentially closed by the body 214. However, once the plunger is moved into a second, dosing position, indicated in FIG. 3B at 340b, the lower opening 348b is disposed along the second inhalation channel 252. When airflow through the second inhalation channel 252 is established, air passes through the upper opening 248a, through the dosing chamber 344 and through the lower opening 348b, thereby entraining the medicament carried in the dosing chamber and carrying it to the user. As shown in FIG. 3B, a screen or shield 354 may also be provided to prevent airborne materials from being sucked into the dosing chamber 344 or secondary inhalation channel during inhalation.

In use, the medicament inhalator 310 shown in FIGS. 3A and 3B operates in substantially the same manner as the medicament inhalator 210 shown in FIGS. 2A through 2C, with the exception of the initial act making the medicament available for inhalation. With the medicament inhalator 210 of FIGS. 2A through 2C, the user initially places the tape 260 in the opening 252a in the secondary inhalation channel 252 and then presses on the lancet 218 so that the sharp projection 270 punctures the medicament-filled blister 268. With the medicament inhalator 310 of FIGS. 3A and 3B, the dosing plunger 340 is moved into the first, refill position 340a to allow medicament 334 from the bulk medicament cartridge 320 to fill the dosing chamber 344. The plunger 340 is then advanced into the dosing position 340b, wherein the dosing chamber 344 is disposed in fluid communication with the secondary inhalation passage.

The user breathes in the same manner with either medicament inhalator, and the rotatable vane 240 moves from the initial position 240a (FIGS. 2A, 3A and 3B) into the intermediate position 240b (FIG. 2B) and into the final position 240c (FIG. 2C). The movement of the rotatable vane 240 moves the blocking plate 280, thereby placing the second inhalation channel 252 in communication with the distal portion 234b of the first inhalation channel 226, thereby supplying medicament to the user.

While numerous devices could be provided to determine when the bulk medicament cartridge 320 is empty, the simplest mechanism for ensuring that medicament is present is to provide a bulk medicament cartridge which is transparent. Once the user can no longer see the medicament in the bulk medicament cartridge 320, the cartridge can be unscrewed from the top 324 and replaced with a new cartridge. Of course, those skilled in the art will appreciate that the medicament inhalator 310 could be easily adapted for use with other types of bulk medicament cartridges.

In addition to the benefits discussed above, the present invention overcomes another common cause of agglomeration of medicament and/or carrier particles. A user will sometimes accidentally blow into the mouthpiece rather than inhaling through the mouthpiece as intended. This results in very humid air moving into the dry powder medicament (either a blister that has been punctured or a reservoir-type medicament storage container) which promotes agglomeration of the medicament particles and/or medicament/carrier particles.

The present invention, however, avoids this problem. The blocking plate 84 (FIGS. 1–1C) or 280 (FIGS. 2A–3B) maintains the medicament in position where it is isolated from the user's breath. Thus, even if the user were to completely exhale through the primary inhalation passage 60 (FIGS. 1–1C) or 220 (FIGS. 2A–3B), the exhaled air would not come in contact with the medicament and would not cause agglomeration.

Thus there is disclosed an improved dry powder medicament inhalator having an inhalation-activated flow diverting means for triggering delivery of medicament. Those skilled in the art will recognize numerous modifications which may be made without departing from the scope or spirit of the present invention. The appended claims are intended to cover such modifications.

What is claimed is:

1. A dry powder medicament inhalator comprising:
a housing including a body having:
   a medicament cartridge receiving cavity formed within the housing;
   a medicament cartridge disposed at least partially within the cavity, the medicament cartridge being configured for holding bulk medicament;
   a dosing plunger configured for disposing medicament in the secondary inhalation passage to facilitate entrainment of the medicament in air flowing through the secondary inhalation passage when the blocking means is disposed in the second, open position,
   a primary inhalation passage extending through the body for allowing airflow through the body;
   a rotatable flow restricting means disposed in the primary inhalation passage such that air passing through the primary inhalation passage moves the rotatable flow restricting means between a first, open position, wherein the rotatable flow restricting means does not substantially inhibit airflow through the primary inhalation passage, and a second, restricting position wherein the rotatable flow restricting means restricts airflow through the primary inhalation passage;
   a secondary inhalation passage extending at least partially through the body, the secondary inhalation passage being disposed in communication with the medicament cartridge receiving cavity; and
   blocking means for selectively preventing airflow through the secondary inhalation passage, the blocking means being biased in a first, closed position to block airflow through the secondary inhalation passage and disposed in communication with the rotatable flow restricting means such that movement of the rotatable flow restricting means from the first, open position to the second, restricting position moves the blocking means from the first, closed position to a second, open position, and thereby permits airflow through the secondary inhalation passage.

2. The apparatus of claim 1, further comprising a spring means disposed in communication with the rotatable airflow restricting means and the blocking means for biasing the rotatable airflow restricting means and the blocking means into their respective first positions.

3. The apparatus of claim 1, wherein the primary inhalation passage has an open proximal end and an open distal end, and therein the rotatable flow restriction means is disposed between the proximal end and the distal end to thereby divide the primary inhalation passage into a proximal portion and a distal portion.

4. The apparatus of claim 3, wherein the secondary inhalation passage is disposed in communication with the primary inhalation passage between the rotatable flow restriction means and the distal end.

5. The apparatus of claim 1, wherein the cavity is disposed in fluid communication with the secondary inhalation passage such that medicament disposed within the cavity is entrained in air passing through the secondary inhalation passage when the blocking means is disposed in the second, open position.

6. The medicament inhalator of claim 1, wherein the dosing plunger has a dosing chamber formed therein for receiving medicament, and wherein the dosing plunger is slidable between a refill position, wherein the medicament from the cartridge fills the dosing chamber, and a dosing position, wherein the dosing chamber is disposed in fluid communication with the secondary inhalation passage.

7. The medicament inhalator of claim 1, wherein the secondary inhalation passage includes a substantially nonlinear channel.

8. The medicament inhalator of claim 7, wherein the secondary inhalation passage includes an impact surface disposed therealong and positioned to be impacted by agglomerated medicament entrained in air flowing through the secondary inhalation passage to thereby break up the agglomeration.

9. The medicament inhalator of claim 7, wherein the secondary inhalation passage includes an impact surface disposed therealong and positioned to be impacted by medicament/carrier particles entrained in air flowing through the secondary inhalation passage to thereby facilitate removal of medicament particles from carrier particles.

10. The medicament inhalator of claim 1, wherein the housing further includes a top pivotably attached to the body, and wherein the medicament cartridge receiving cavity is disposed between the top and the body.

11. The medicament inhalator of claim 10, wherein the secondary inhalation passage extends through the top and through a sufficient part of the body to open into the primary inhalation passage.

12. The medicament inhalator of claim 1, wherein the rotatable flow restricting means is rotatable into a third position beyond the second position, wherein the rotatable flow restricting means restricts airflow through the primary inhalation passage, but to a lesser degree than when the rotatable vane in disposed in the second position.

13. A medicament inhalator for selectively administering medicament, the medicament inhalator comprising:
   a housing having a body with an open proximal end and an open distal end;
   a primary inhalation passage extending from the open proximal end to the open distal end;
   a rotatable vane disposed in the primary inhalation passage between the open proximal end and the open distal end;
   a secondary inhalation passage extending partially through the body to an opening into the primary inhalation passage between the rotatable vane and the distal end;
   a blocking plate disposed to selectively prevent airflow from the secondary inhalation passage into the primary inhalation passage, the blocking plate having a first, closed position wherein the blocking plate prevents airflow from the secondary inhalation passage into the primary inhalation passage, and a second, open position, wherein the blocking plate does not prevent airflow from the secondary inhalation passage into the primary inhalation passage; and
   means for selectively moving the blocking plate into the second, open position when a user inhales through the primary inhalation passage.

14. The medicament inhalator of claim 12, wherein the means for selectively moving the blocking plate comprises a rotatable vane disposed in the primary inhalation passage.

15. The medicament inhalator of claim 14, wherein the rotatable vane is rotatable between a first position, wherein the rotatable vane provides minimal interference to airflow from the proximal end to the distal end of the primary inhalation passage, and a second position, wherein the rotatable vane substantially inhibits airflow from the proximal end to the distal end of the primary inhalation passage.

16. The medicament inhalator of claim 15, wherein rotation of the rotatable vane into the second position, moves the blocking plate into the second, open position, to thereby enable airflow through the secondary inhalation passage.

17. The medicament inhalator of claim 16, further comprising biasing means for biasing the rotatable vane and the blocking plate in their respective first positions.

18. The medicament inhalator of claim 12, wherein the medicament inhalator further comprises a cavity for receiving medicament, the cavity being disposed in fluid communication with the secondary inhalation passage.

19. A method for preventing agglomeration of medicament in an inhalator, the method comprises;
   (a) providing a housing having a body with an open proximal end and an open distal end, the body defining a primary inhalation passage extending from the open proximal end to the open distal end and a secondary inhalation passage extending partially through the body to an opening into the primary inhalation passage;
   (b) disposing a blocking means between the primary and secondary inhalation passages such that the blocking means has a first, closed position wherein the blocking means prevents fluid flow between the primary inhalation passage and the secondary inhalation passage, and a second, open position wherein the blocking means does not prevent fluid flow between the primary inhalation passage and the secondary inhalation passage; and
   (c) biasing the blocking means into the first, closed position such that primary and secondary inhalation passages are only disposed in fluid communication when a user inhales through the primary inhalation channel.

20. The method according to claim 19, wherein the method further comprises disposing an actuator means in the primary inhalation passage and in communication with the blocking means, and disposing the actuator member such that inhalation through the primary inhalation passage moves the actuator member, thereby moving the blocking means into the second, open position.

21. The method according to claim 20, wherein the method further comprises, disposing actuator means such that movement of the actuator means by inhalation inhibits airflow through the primary inhalation passage.

22. A method for improving deposition of medicament in the lungs of an inhalator user, the method comprising;
   (a) providing a housing having a body with an open proximal end and an open distal end, the body defining a primary inhalation passage extending from the open proximal end to the open distal end and a means for selectively releasing medicament into the primary inhalation passage;
   (b) disposing a inhibiting means in the primary inhalation passage to selectively restrict airflow through the primary inhalation passage; and
   (c) connecting the inhibiting means to the means for selectively releasing medicament such that medicament is released into the primary inhalation passage only when the inhibiting means is restricting airflow through the primary inhalation passage.

23. The method according to claim 22, wherein the method further comprises selectively restricting airflow through the primary inhalation passage to prolong inhalation by the inhalator user after medicament is released into the primary inhalation passage.

24. A method for increasing the deep lung deposition of medicament, the method comprising:
   (a) providing an inhalator having a primary inhalation passage, a means for releasing medicament into the primary inhalation passage and a movable means for restricting airflow through the primary inhalation passage;
   (b) inhaling through the primary inhalation passage at a first rate;
   (c) moving the movable means for restricting airflow through the primary inhalation passage to restrict airflow through the primary inhalation passage and thereby slow the rate of inhalation through the primary inhalation passage to a second rate;
   (d) waiting to release medicament into the primary inhalation passage until the rate of inhalation has been slowed to the second rate: and
   (e) releasing medicament into the primary inhalation passage while airflow through the primary inhalation passage is inhibited to slow inhalation to the second rate.

25. The method according to claim 24, wherein the method further comprises maintaining the movable means for restrictive airflow in an airflow restricting position until inhalation is complete.

* * * * *

UNITED STATES PATENT AND TRADEMARK OFFICE
CERTIFICATE OF CORRECTION

PATENT NO. : 5,988,163
DATED : November 23, 1999
INVENTOR(S) : Casper et al.

It is certified that error appears in the above-identified patent and that said Letters Patent is hereby corrected as shown below:

Title page,
Item [60], Related U.S. Application Data, should read
-- [60] Provisional application No. 60/001,786, Aug. 2, 1995. --.

Column 1,
Line 14, should read -- Ser. No. 60/001,786, filed on Aug. 2, 1995 --.

Signed and Sealed this

Sixth Day of September, 2005

JON W. DUDAS
*Director of the United States Patent and Trademark Office*